US012629202B2

(12) United States Patent
Kastelein et al.

(10) Patent No.: US 12,629,202 B2
(45) Date of Patent: May 19, 2026

(54) MAGNETICALLY STEERABLE IRRIGATED ABLATION CATHETERS, AND SYSTEMS AND METHODS THEREOF

(71) Applicant: Stereotaxis, Inc., St. Louis, MO (US)

(72) Inventors: Nathan Kastelein, Troy, IL (US); Paul F. Rebillot, III, St. Louis, MO (US); Wilfred Peter Heiner, Rheinfelden (DE); Emre Güntav, Cologne (DE)

(73) Assignee: Stereotaxis, Inc., St. Louis, MO (US)

( * ) Notice: Subject to any disclaimer, the term of this patent is extended or adjusted under 35 U.S.C. 154(b) by 711 days.

(21) Appl. No.: 17/899,320

(22) Filed: Aug. 30, 2022

(65) Prior Publication Data

US 2023/0068563 A1     Mar. 2, 2023

Related U.S. Application Data

(60) Provisional application No. 63/238,304, filed on Aug. 30, 2021.

(51) Int. Cl.
A61B 18/14 (2006.01)
A61B 18/00 (2006.01)
(52) U.S. Cl.
CPC ............................... A61B 18/1492 (2013.01); *A61B 2018/00351* (2013.01); *A61B 2018/00577* (2013.01); *A61B 2218/002* (2013.01)
(58) Field of Classification Search
CPC ...... A61B 18/1492; A61B 2018/00351; A61B 2018/00577; A61B 2218/002
See application file for complete search history.

(56) References Cited

U.S. PATENT DOCUMENTS

| | | | |
|---|---|---|---|
| 5,500,012 | A | 3/1996 | Brucker et al. |
| 5,779,731 | A | 7/1998 | Leavitt |
| 5,871,523 | A | 2/1999 | Fleischman et al. |

(Continued)

FOREIGN PATENT DOCUMENTS

| | | |
|---|---|---|
| WO | WO-2004103436 A2 | 12/2004 |
| WO | WO-2023034319 A1 | 3/2023 |

OTHER PUBLICATIONS

International Preliminary Report on Patentability for International Application No. PCT/US2022/042065 mailed Mar. 14, 2024, 12 pages.

(Continued)

*Primary Examiner* — Linda C Dvorak
*Assistant Examiner* — Abigail Bock
(74) *Attorney, Agent, or Firm* — Cooley LLP

(57)     ABSTRACT

Embodiments described herein relate to magnetically steerable irrigated ablation catheters and methods of operating the same. A steerable catheter can include a distal tip including a first set of magnets. The steerable catheter further includes a shaft. The shaft includes a flexible section with a distal end coupled to the distal tip. The shaft further includes a second set of magnets spaced along a length of the flexible section and spaced from the first set of magnets such that the first and second sets of magnets collectively enable the flexible section to curve without kinking in response to a magnetic field being applied to the first and second set of magnets. In some embodiments, each magnet from the second set of magnets can be coupled to the flexible section via metallic elements disposed at the ends of each magnet.

14 Claims, 9 Drawing Sheets

(56)            References Cited

U.S. PATENT DOCUMENTS

| | | | |
|---|---|---|---|
| 5,904,147 | A | 5/1999 | Conlan et al. |
| 6,181,973 | B1 | 1/2001 | Ceron et al. |
| 6,358,256 | B1 | 3/2002 | Reinhardt |
| 6,517,534 | B1 | 2/2003 | Mcgovern et al. |
| 6,522,909 | B1 | 2/2003 | Garibaldi et al. |
| 6,662,034 | B2 | 12/2003 | Segner et al. |
| 6,783,542 | B2 | 8/2004 | Eidenschink |
| 6,911,019 | B2 | 6/2005 | Mulier et al. |
| 7,066,924 | B1 | 6/2006 | Garibaldi et al. |
| 7,105,981 | B2 | 9/2006 | Lazenby |
| 7,393,339 | B2 | 7/2008 | Zawacki et al. |
| 7,653,426 | B2 | 1/2010 | Yatsuo et al. |
| 7,869,854 | B2 | 1/2011 | Shachar et al. |
| 7,873,401 | B2 | 1/2011 | Shachar |
| 7,873,402 | B2 | 1/2011 | Shachar |
| 7,914,517 | B2 | 3/2011 | Baran et al. |
| 7,930,014 | B2 | 4/2011 | Huennekens et al. |
| 7,998,184 | B2 | 8/2011 | Eidenschink |
| 8,027,714 | B2 | 9/2011 | Shachar |
| 8,152,951 | B2 | 4/2012 | Zawacki et al. |
| 8,192,399 | B2 | 6/2012 | Birchard |
| 8,287,532 | B2 | 10/2012 | Carroll et al. |
| 8,457,714 | B2 | 6/2013 | Shachar et al. |
| 8,480,653 | B2 | 7/2013 | Birchard et al. |
| 8,532,743 | B2 | 9/2013 | Stangenes et al. |
| 8,702,619 | B2 | 4/2014 | Wang |
| 8,734,502 | B2 | 5/2014 | Orr |
| 8,808,227 | B2 | 8/2014 | Zawacki et al. |
| 8,827,910 | B2 | 9/2014 | De La Rama et al. |
| 8,911,491 | B2 | 12/2014 | Hanson et al. |
| 8,979,840 | B2 | 3/2015 | Christian |
| 9,014,821 | B2 | 4/2015 | Wang |
| 9,017,283 | B2 | 4/2015 | Birchard et al. |
| RE45,534 | E | 6/2015 | Huennekens et al. |
| 9,186,209 | B2 | 11/2015 | Weber et al. |
| 9,314,327 | B2 | 4/2016 | Orr |
| 9,314,589 | B2 | 4/2016 | O'Day et al. |
| 9,375,154 | B2 | 6/2016 | Wang |
| 9,381,063 | B2 | 7/2016 | Gang et al. |
| 9,387,304 | B2 | 7/2016 | Zawacki et al. |
| 9,463,302 | B2 | 10/2016 | Stangenes et al. |
| 9,545,263 | B2 | 1/2017 | Lenihan et al. |
| 9,579,198 | B2 | 2/2017 | Deem et al. |
| 9,655,539 | B2 | 5/2017 | Shachar et al. |
| 9,723,998 | B2 | 8/2017 | Wang |
| 9,743,845 | B2 | 8/2017 | Wang |
| 9,743,992 | B2 | 8/2017 | Stigall et al. |
| RE46,562 | E | 10/2017 | Huennekens et al. |
| 9,801,683 | B2 | 10/2017 | Stangenes et al. |
| 9,820,811 | B2 | 11/2017 | Wang |
| 9,861,438 | B2 | 1/2018 | Govari |
| 9,919,131 | B2 | 3/2018 | Birchard et al. |
| 9,949,793 | B2 | 4/2018 | Olson et al. |
| 10,111,708 | B2 | 10/2018 | Wang |
| 10,159,586 | B2 | 12/2018 | Helmick et al. |
| 10,226,203 | B2 | 3/2019 | Stigall et al. |
| 10,258,468 | B2 | 4/2019 | Deem et al. |
| 10,290,230 | B2 | 5/2019 | Babiker et al. |
| 10,543,308 | B2 | 1/2020 | Lenihan et al. |
| 10,561,473 | B2 | 2/2020 | Stigall et al. |
| 10,596,356 | B2 | 3/2020 | Lenihan et al. |
| 10,722,303 | B2 | 7/2020 | Wang |
| 10,842,559 | B2 | 11/2020 | Wang |
| 2004/0231683 | A1* | 11/2004 | Eng ........................ A61B 34/73 <br> 606/41 |
| 2006/0144407 | A1* | 7/2006 | Aliberto ............ A61M 25/0127 <br> 600/431 |
| 2008/0091193 | A1* | 4/2008 | Kauphusman ..... A61B 18/1492 <br> 606/41 |

OTHER PUBLICATIONS

International Search Report and Written Opinion for International Application No. PCT/US2022/042065 dated Jan. 23, 2023, 20 Pages.

* cited by examiner

FIG. 1

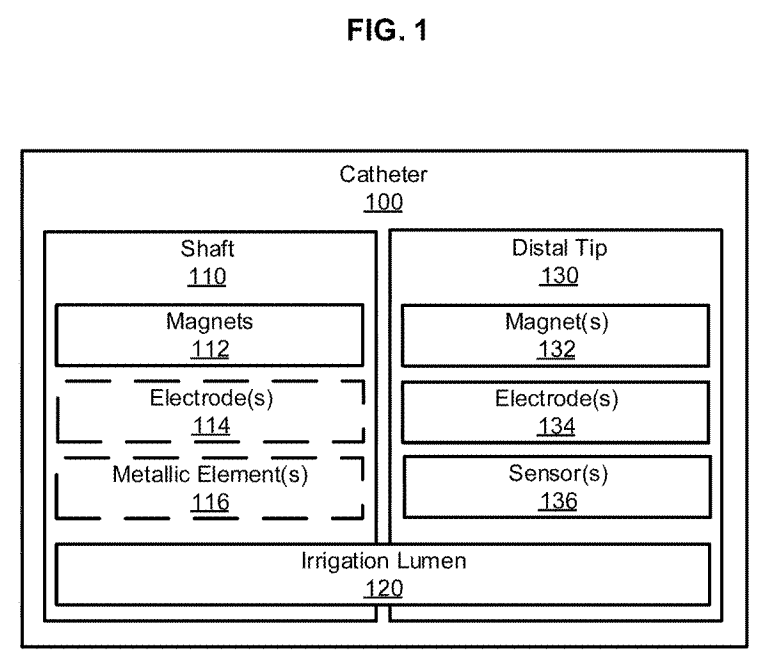

Catheter
100

Distal Tip
130

Magnet(s)
132

Electrode(s)
134

Sensor(s)
136

Shaft
110

Magnets
112

Electrode(s)
114

Metallic Element(s)
116

Irrigation Lumen
120

MAGNETICALLY STEERABLE IRRIGATED ABLATION CATHETERS, AND SYSTEMS AND METHODS THEREOF

CROSS REFERENCE TO RELATED APPLICATIONS

This application claims the benefit of U.S. Provisional Application No. 63/238,304, titled, "Magnetically Steerable Irrigated Ablation Catheter," and filed Aug. 30, 2021, the content of which is incorporated herein by reference in its entirety.

TECHNICAL FIELD

Embodiments described herein generally relate to magnetically steerable irrigated ablation catheters and methods of operating the same.

BACKGROUND

Interventional or surgical procedures can involve navigation of catheters and other medical devices through a vessel, lumen, or other space within patient anatomy. For example, catheterization is a common practice for electrophysiology mapping, ablation, and/or other medical procedures. During catheterization, thin, flexible tubes with sensing and/or treatment elements can enter the vasculature of the patient and be guided to a target site (e.g., a cardiac chamber of a heart). Conventional methods of catheter movement and control of such movement can often be imprecise, and can lead to undesired contact with patient anatomy or undesired placement of a catheter. Such undesired outcomes can lead to complications, such as improper positioning for application of treatment (e.g., ablation) and/or measurement of electrophysiological signals. Precise control of the catheter movement can aid in preventing these issues.

SUMMARY

Embodiments described herein relate to magnetically steerable irrigated ablation catheters and methods of operating the same. A steerable catheter can include a distal tip including a first set of magnets. The steerable catheter further includes a shaft. The shaft includes a flexible section with a distal end coupled to the distal tip. The shaft further includes a second set of magnets spaced along a length of the flexible section and spaced from the first set of magnets such that the first and second sets of magnets collectively enable the flexible section to curve without kinking in response to a magnetic field being applied to the first and second set of magnets. In some embodiments, each magnet from the second set of magnets can be coupled to one or more coils via metallic elements disposed at the ends of each magnet. In some embodiments, each metallic element can be formed of a ferromagnetic material. In some embodiments, each magnet from the first and second set of magnets can include a neodymium iron boron magnet.

BRIEF DESCRIPTION OF THE DRAWINGS

FIG. 1 is a block diagram of a magnetically steerable catheter, according to an embodiment.

FIGS. 7A-7B show a distal tip of a magnetically steerable catheter, according to an embodiment.

DETAILED DESCRIPTION

Figure 2:
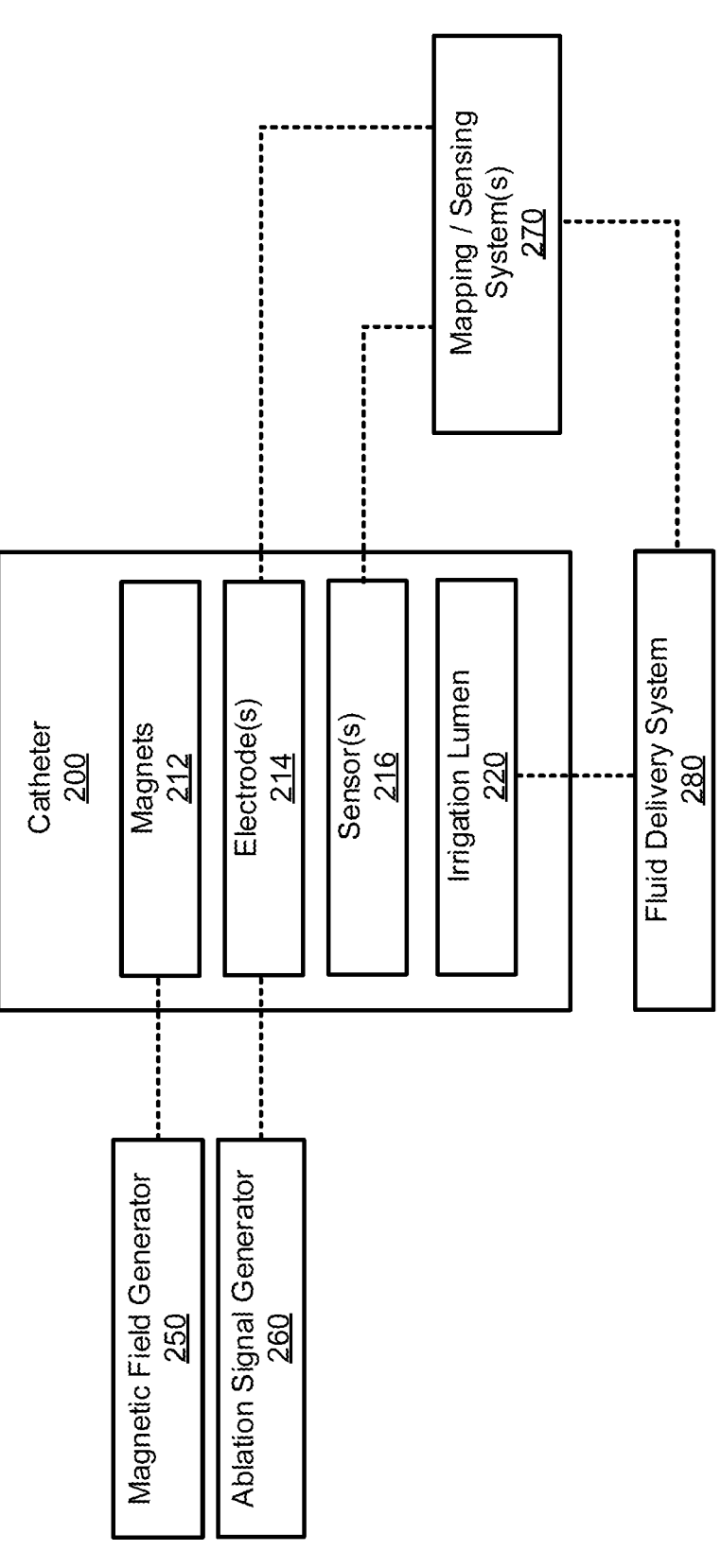
FIG. 2 is a block diagram of a guiding system including a magnetically steerable catheter, according to an embodiment.

Embodiments described herein relate to magnetically steerable catheters and methods of operating the same. Catheters as described herein include a shaft with magnets dispersed thereon. Such catheters can be moved by applying an external magnetic field. As such, such catheters can be navigated within patient anatomy by generating magnetic fields with specific field lines that interact with the magnets dispersed along the catheter. In some embodiments, a plurality of magnets can be disposed along the catheter with flexible sections of the catheter disposed between adjacent magnets. With a sufficient number of magnets that are evenly distributed, e.g., to enable the catheter to curve, the catheter can be finely and precisely controlled. This fine control can make the catheter more easily able to enter difficult-to-reach locations in patient anatomy, such as, for example, a patient's vasculature and/or cardiac anatomy. The catheters described herein, as they are capable of being magnetically steered, also remove the need for proximally actuated steering or bending mechanisms. This can help improve stability of the catheter and/or reduce a lateral profile or size of the catheter. The magnetic steering can also improve deflection and side-force compared to other types of steerable catheters. Balancing mechanical and magnetic forces can allow for consistent contact and temperature monitoring during intracardiac ablation for precise stimulation of the heart.

In addition to the magnets providing steerability, electrodes can be placed along an elongate shaft of the catheter (e.g., near the magnets) and/or at a distal end of the catheter. Electrodes placed throughout the shaft can deliver high spatial resolution in the heart, and electrodes placed at a distal tip of the catheter can be used for electrophysiological monitoring, ablation, etc. The catheter can be used in combination with a signal generator for generating ablation signals, a mapping system, and/or a fluid delivery system, as further detailed below. In some embodiments, the catheter can include automatic advancement and/or retraction systems, various guiding sheaths, deployable elements, etc.

FIG. 1 is a block diagram of a magnetically steerable catheter 100, according to an embodiment. As shown, the catheter 100 includes a shaft 110 and a distal tip 130. The catheter 100 can include an irrigation lumen 120 that extends from a proximal end of the catheter 100 to the distal tip 130. The shaft 110 includes a plurality of magnets 112. Optionally, the shaft 110 can include one or more electrodes 114 and one or more metallic elements 116. The distal tip 130 includes one or more magnets 132, one or more electrodes 134, and one or more sensors 136. In some embodiments, the catheter 100 can be advanced and retracted via a catheter advancement system (not depicted). In some embodiments, the catheter 100 can be an ablation catheter. In some embodiments, the catheter 100 can be a mapping or sensing catheter, such as, for example, an electrophysiology catheter. In some embodiments, the catheter 100 can be a single use catheter. In some embodiments, the catheter 100 can be a reusable catheter.

In some embodiments, the catheter 100 can be delivered through a sheath into target anatomy. For example, a guiding sheath can be placed within patient anatomy (e.g., a femoral vein), and the catheter 100 can be advanced through the sheath to the target anatomy (e.g., the heart). In such instances, the catheter 100 can be sufficiently flexible such that the catheter 100 can be advanced along a length of the sheath, including, for example, through curves and/or more tortuous pathways. In some embodiments, the distal tip 130 of the catheter 100 can include multiple magnets that are separated by a flexible section such that the distal tip 130 can curve and/or flex sufficiently to allow the distal tip 130 to advance along the sheath without creating high amounts of friction.

The shaft 110 can be flexible such that the shaft 110 can be steered via the magnets 112 and/or magnet(s) 132 along a predetermined pathway within patient anatomy. In some embodiments, the shaft 110 can have a braided shaft design. In some embodiments, the shaft 110 can include braided and/or extruded polymers. In some embodiments, braided and/or extruded polymers can be laminated together to form the shaft 110. In some embodiments, the shaft 110 can include extruded polymers with varying softness. In some embodiments, the shaft 110 can have a coiled structure. For example, the shaft 110 can have a helical structure, such as a material that winds around a central axis in a pattern similar to a corkscrew or spiral staircase. In some embodiments, the coiled structure can include stainless steel and/or aluminum. In some embodiments, the coiled structure can be covered with a coating. In some embodiments, the coating can be composed of a polymer, an elastomer, a polyamide, Zytel®, Rilsan®, Grilamid®, Vestamid®, Pebax®, or any combination thereof. In some embodiments, the shaft 110 can gradually transition from one material to the next to vary flexibility along a length of the shaft 110 and/or to reduce discontinuities in the structure of the catheter 100.

In some embodiments, the shaft 110 can have a diameter of about 6 Fr to about 10 Fr, inclusive of all values and subranges therebetween. In some embodiments, the shaft 110 can have a length of at least about 50 cm, at least about 60 cm, at least about 70 cm, at least about 80 cm, at least about 90 cm, at least about 100 cm, at least about 110 cm, at least about 120 cm, at least about 130 cm, at least about 140 cm, at least about 150 cm, at least about 160 cm, at least about 170 cm, at least about 180 cm, or at least about 190 cm. In some embodiments, the shaft 110 can have a length of no more than about 200 cm, no more than about 190 cm, no more than about 180 cm, no more than about 170 cm, no more than about 160 cm, no more than about 150 cm, no more than about 140 cm, no more than about 130 cm, no more than about 120 cm, no more than about 110 cm, no more than about 100 cm, no more than about 90 cm, no more than about 80 cm, no more than about 70 cm, or no more than about 60 cm. Combinations of the above-referenced lengths of the shaft 110 are also possible (e.g., at least about 50 cm and no more than about 200 cm or at least about 100 cm and no more than about 150 cm), inclusive of all values and ranges therebetween. In some embodiments, the shaft 110 can have a length of about 50 cm, about 60 cm, about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, or about 200 cm.

The magnets 112 are distributed throughout the shaft 110. In some embodiments, the magnets 112 can be distributed evenly or substantially evenly along the length of the shaft 110. In some embodiments, the magnets 112 can have a cylindrical shape or a hollow cylinder shape (e.g., such that the magnets 112 can be disposed around an inner core or structure of the shaft, e.g., the irrigation lumen 120). Alternatively, the magnets 112 can be non-cylindrical (e.g., a block, bead, or arc shape) and can be discretely disposed at different positions (e.g., angular positions) about a circumference of the shaft 110.

Coils in the shaft 110 and the magnets 112 can allow precise navigation to the target anatomy (e.g., the heart). For example, the navigation profile of the catheter 100 can be smoother and more flexible with more magnets 112. In some embodiments, the magnets 112 can include a sufficient number of magnets that are distributed through a length of the shaft 110 such that substantial deflection changes can be prevented as each magnet 112 exits a sheath or other delivery structure. In some embodiments, the catheter 100 can include at least about 3 magnets 112, at least about 4 magnets 112, at least about 5 magnets 112, at least about 6 magnets 112, at least about 7 magnets 112, at least about 8 magnets 112, at least about 9 magnets 112, at least about 10 magnets 112, at least about 15 magnets 112, at least about 20 magnets 112, at least about 25 magnets 112, at least about 30 magnets 112, at least about 35 magnets 112, at least about 40 magnets 112, at least about 45 magnets 112, at least about 50 magnets 112, at least about 55 magnets 112, at least about 60 magnets 112, at least about 65 magnets 112, at least about 70 magnets 112, at least about 75 magnets 112, at least about 80 magnets 112, at least about 85 magnets 112, at least about 90 magnets 112, or at least about 95 magnets 112. In some embodiments, the catheter 100 can include no more than about 100 magnets 112, no more than about 95 magnets 112, no more than about 90 magnets 112, no more than about 85 magnets 112, no more than about 80 magnets 112, no more than about 75 magnets 112, no more than about 70 magnets 112, no more than about 65 magnets 112, no more than about 60 magnets 112, no more than about 55 magnets 112, no more than about 50 magnets 112, no more than about 45 magnets 112, no more than about 40 magnets 112, no more than about 35 magnets 112, no more than about 30 magnets 112, no more than about 25 magnets 112, no more than about 20 magnets 112, no more than about 15 magnets 112, no more than about 10 magnets 112, no more than about 9 magnets 112, no more than about 8 magnets 112, no more than about 7 magnets 112, no more than about 6 magnets 112, no more than about 5 magnets 112, no more than about 4 magnets 112, or no more than about 3 magnets 112.

Combinations of the above-referenced numbers of magnets 112 are also possible (e.g., at least about 5 magnets 112 and no more than about 20 magnets 112), inclusive of all values and ranges therebetween. In some embodiments, the catheter 100 can include about 3 magnets 112, about 4 magnets 112, about 5 magnets 112, about 6 magnets 112, about 7 magnets 112, about 8 magnets 112, about 9 magnets 112, about 10 magnets 112, about 15 magnets 112, about 20 magnets 112, about 25 magnets 112, about 30 magnets 112, about 35 magnets 112, about 40 magnets 112, about 45 magnets 112, about 50 magnets 112, about 55 magnets 112, about 60 magnets 112, about 65 magnets 112, about 70 magnets 112, about 75 magnets 112, about 80 magnets 112, about 85 magnets 112, about 90 magnets 112, about 95 magnets 112, or about 100 magnets 112.

In some embodiments, the magnets 112 can each have a length along the shaft 110 of at least about 1 mm, at least about 2 mm, at least about 3 mm, at least about 4 mm, and at least about 5 mm, at least about 6 mm, at least about 7 mm, at least about 8 mm, at least about 9 mm, or at least about 10 mm. In some embodiments, the magnets 112 can each have a length along the shaft 110 of no more than about 10 mm, no more than about 9 mm, no more than about 8 mm, no more than about 7 mm, no more than about 6 mm, no more than about 5 mm, no more than about 4 mm, no more than about 3 mm, or no more than about 2 mm. Combinations of the above-referenced lengths of the magnets 112 are also possible (e.g., at least about 1 mm and no more than about 10 mm), inclusive of all values and ranges therebetween. In some embodiments, the magnets 112 can each have a length along the shaft 110 of about 1 mm, about 2 mm, about 3 mm, about 4 mm, about 5 mm, about 6 mm, about 7 mm, about 8 mm, about 9 mm, or about 10 mm. In some embodiments, each of the magnets 112 can have the same or substantially similar lengths along the length of the shaft 110. In some embodiments, one or more of the magnets 112 can have different lengths along the length of the shaft 110.

In some embodiments, the magnets 112 and/or magnet(s) 132 can be spaced apart along a length of the catheter 100 to allow the catheter 100 to develop a desired radius of curvature. In some embodiments, the catheter 100 can be used for cardiac electrophysiology mapping and/or cardiac ablation procedures. For example, the catheter 100 can be used to treat cardiac arrhythmias, including, for example, atrial fibrillation. In some embodiments, the catheter 100 can be navigated to a cardiac chamber of a heart, e.g., the left atrial chamber including its associated pulmonary veins. In some embodiments, the distal portion of the catheter 100 (e.g., the portion including the magnets 112, 132) can be configured to fit within the cardiac chamber of the heart (e.g., the left atrial chamber) when the catheter is in a curved configuration (e.g., in a fully curved configuration). The distal portion of the catheter 100 can be configured to curve without having any discontinuities. In some embodiments, the distal portion of the catheter 100 can have sections that curve about different axes (i.e., have a plurality of concave or convex curves). In some embodiments, the distal portion of the catheter 100 can curve to position the distal tip 130 at or near an entryway into a pulmonary vein. In some embodiments, one or more sections of the catheter 100 can be configured to have a radius of curvature suitable for navigation and/or positioning within a cardiac chamber of a heart (e.g., a left atrium of a heart). In some embodiments, the radius of curvature of one or more sections of the catheter 100 can be adjusted during use of the catheter 100.

In some embodiments, one or more sections of the distal portion of the catheter 100 can have a radius of curvature of at least about 4 mm, at least about 5 mm, at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, at least about 17 mm, at least about 18 mm, at least about 19 mm, at least about 20 mm, at least about 21 mm, at least about 22 mm, at least about 23 mm, or at least about 24 mm. In some embodiments, one or more sections of the distal portion of the catheter 100 can have a radius of curvature of no more than about 25 mm, no more than about 24 mm, no more than about 23 mm, no more than about 22 mm, no more than about 21 mm, no more than about 20 mm, no more than about 19 mm, no more than about 18 mm, no more than about 17 mm, no more than about 16 mm, no more than about 15 mm, no more than about 14 mm, no more than about 13 mm, no more than about 12 mm, no more than about 11 mm, no more than about 10 mm, no more than about 9 mm, no more than about 8 mm, no more than about 7 mm, no more than about 6 mm, or no more than about 5 mm. Combinations of the above-referenced radii of curvature are also possible (e.g., at least about 4 mm and no more than about 25 mm or at least about 10 mm and no more than about 20 mm), inclusive of all values and ranges therebetween. In some embodiments, one or more sections of the distal portion of the catheter 100 can have a radius of curvature of about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm. In an embodiment, the distal portion of the catheter 100 can have sections with radius of curvature between about 4 mm and about 25 mm, inclusive of all values and sub ranges therebetween.

In some embodiments, the catheter 100 can have a radius of curvature that changes along the length of the catheter 100. For example, the catheter 100 can have a first section with a first radius of curvature and a second section with a second radius of curvature, the second radius of curvature different from the first radius of curvature. In some embodiments, the radius of curvature of the catheter 100 can change gradually along the length of the catheter 100. In some embodiments, the catheter 100 can have a compound curve shape, e.g., have sections that form a curve with varying circular arcs. For example, the catheter 100 can have a distal portion that has an S shape. In other words, the catheter 100 can have a first section that curves in a first direction and a second section that curves in a second direction, the second direction different from the first section.

In some embodiments, the catheter 100 or at least a portion of the catheter 100 (e.g., a distal portion of the catheter 100 including the distal tip 130) can be configured to have a radius of curvature that allows at least the portion of the catheter 100 to curve and contact target anatomy (e.g., the walls of a pulmonary vein). The catheter 100 can be advanced in a minimally invasive fashion through vasculature to a target location within the heart. The catheter 100 can be introduced, e.g., via a sheath, into a patient's vasculature (e.g., the femoral vein). The catheter 100 can then be steered via the patient's vasculature to the heart chamber. In particular, the catheter 100 can be navigated using the magnets 112 and/or magnet(s) 132. Once positioned within the heart, the catheter 100 can be used to perform mapping and/or ablation, e.g., via electrode(s) 134 disposed on the distal tip 130 of the catheter 100.

Spacing of the magnets 112 can be selected to increase the steering capability of the catheter 100. By placing the magnets 112 too close to each other, the catheter 100 can have difficulty curving. By placing the magnets 112 too far apart, steering the catheter 100 can become difficult (e.g., lead to sharp bends or discontinuities in the catheter 100 and/or sudden directional changes in the catheter 100). In some embodiments, the magnets 112 can be spaced apart by at least about 3 mm, at least about 4 mm, at least about 5 mm, at least about 6 mm, at least about 7 mm, at least about 8 mm, at least about 9 mm, at least about 10 mm, at least about 15 mm, at least about 20 mm, at least about 25 mm, at least about 30 mm, at least about 35 mm, at least about 40 mm, or at least about 45 mm. In some embodiments, the magnets 112 can be spaced apart by no more than about 50 mm, no more than about 45 mm, no more than about 40 mm, no more than about 35 mm, no more than about 30 mm, no more than about 25 mm, no more than about 20 mm, no more than about 15 mm, no more than about 10 mm, no more than about 9 mm, no more than about 8 mm, no more than about 7 mm, no more than about 6 mm, no more than about 5 mm, or no more than about 4 mm. Combinations of the above-referenced spacings between the magnets 112 are also possible (e.g., at least about 3 mm and no more than about 50 mm or at least about 20 mm and no more than about 40 mm), inclusive of all values and ranges therebetween. In some embodiments, the magnets 112 can be spaced apart by about 3 mm, about 4 mm, about 5 mm, about 6 mm, about 7 mm, about 8 mm, about 9 mm, about 10 mm, about 15 mm, about 20 mm, about 25 mm, about 30 mm, about 35 mm, about 40 mm, about 45 mm, or about 50 mm.

In some embodiments, the magnets 112 can be composed of a magnetic material, a ferromagnetic material, or any combination thereof. In some embodiments, the magnets 112 can be composed of neodymium, iron, boron, or any other suitable magnet material or combinations thereof. In some embodiments, the magnets 112 can be coated, e.g., for protection. In some embodiments, the magnets 112 can be coated by a polymer such as, for example, parylene.

The catheter 100 can include electrodes 114 that are disposed along a length of the shaft 110. The electrodes 114 can aid in localization of the shaft 110. For example, with electrodes 114 positioned along a length of the shaft 110, the electrodes 114 can measure an intracardiac signal within the heart with greater resolution. In some embodiments, the electrodes 114 can be placed on different sides of the shaft 110 (e.g., angular positions about a circumference of the shaft 110). The positioning of the electrodes 114 can allow for more precise capture of electrical signals within patient anatomy. For example, depending on the arrangement of the electrodes 114 on the shaft 110, the directionality of the electrodes 114 and signals receive at the electrodes 114 can provide further spatial resolution or greater dimensionality of data. In particular, if a first electrode 114 is placed on the shaft 110 such that the first electrode 114 is facing a front of the patient and a second electrode 114 is placed on the shaft 110 such that the second electrode is facing a back of the patient, signals being captured by the first electrode 114 can indicate to a user that the signal is coming from a front of the patient.

In some embodiments, the electrodes 114 can be disposed adjacent to and/or attached to the magnets 112. For example, the electrodes 114 can be attached to ferromagnetic materials that form and/or couple to the magnets 112. Further details of such an arrangement are provided with respect to FIG. 6 below. In some embodiments, the electrodes 114 include small sensing electrodes or an array of sensing electrodes, such as, for example, button electrodes, pin electrodes, printed electrodes, etc. The small sensing electrodes 114 can have a sensing area (e.g., exposed area) of about 0.5 mm-by-0.5 mm to about 1 mm-by-1 mm, including all values and subranges therebetween. For example, in an embodiment, the small sensing electrodes 114 can have a sensing area of about 0.8 mm-by-0.8 mm, about 0.8 mm-by-0.9 mm, about 0.9 mm-by-0.9 mm, etc. In some embodiments, the electrodes 114 can include annular or ring electrodes disposed around an inner core or support structure (e.g., coils, irrigation lumen 120) of the shaft 110. The ring electrodes 114 can have a diameter of about 6 Fr, about 6.5 Fr, about 7 Fr, about 7.5 Fr, about 8 Fr, about 8.5 Fr, about 9 Fr, about 9.5 Fr, or about 10 Fr, inclusive of all values and ranges therebetween. The ring electrodes 114 can have a length along the shaft 110 of at least about 0.5 mm, at least about 1 mm, at least about 1.5 mm, at least about 2 mm, at least about 2.5 mm, at least about 3 mm, at least about 3.5 mm, at least about 4 mm, or at least about 4.5 mm. In some embodiments, the electrodes 114 can have a length along the shaft 110 or no more than about 5 mm, no more than about 4.5 mm, no more than about 4 mm, no more than about 3.5 mm, no more than about 3 mm, no more than about 2.5 mm, no more than about 2 mm, no more than about 1.5 mm, or no more than about 1 mm. In some embodiments, the electrodes 114 can be composed of one or more of stainless steel, platinum iridium, gold, or another conductive material.

Placement or spacing of the electrodes 114 can affect spatial resolution in the heart. For example, the catheter 100 with electrodes 114 placed closer to each other can capture a bipolar intracardiac with greater spatial resolution than with the electrodes 114 place further apart. Accordingly, use of multiple shaft electrodes 114 placed throughout a length of the shaft 110 can provide physiological data of the patient with greater resolution. In some embodiments, the spacing and/or directionality of the electrodes 114 (e.g., where the electrodes 114 are placed along the shaft 110 and/or the direction the electrodes 114 are facing) can allow the user to determine more precisely where an electrical signal is originating.

In some embodiments, the electrodes 114 can be spaced apart by at least about 3 mm, at least about 4 mm, at least about 5 mm, at least about 6 mm, at least about 7 mm, at least about 8 mm, at least about 9 mm, at least about 10 mm, at least about 15 mm, at least about 20 mm, at least about 25 mm, at least about 30 mm, at least about 35 mm, at least about 40 mm, or at least about 45 mm. In some embodiments, the electrodes 114 can be spaced apart by no more than about 50 mm, no more than about 45 mm, no more than about 40 mm, no more than about 35 mm, no more than about 30 mm, no more than about 25 mm, no more than about 20 mm, no more than about 15 mm, no more than about 10 mm, no more than about 9 mm, no more than about 8 mm, no more than about 7 mm, no more than about 6 mm, no more than about 5 mm, or no more than about 4 mm. Combinations of the above-referenced spacings between the electrodes 114 are also possible (e.g., at least about 3 mm and no more than about 50 mm or at least about 20 mm and no more than about 40 mm), inclusive of all values and ranges therebetween. In some embodiments, the electrodes 114 can be spaced apart by about 3 mm, about 4 mm, about 5 mm, about 6 mm, about 7 mm, about 8 mm, about 9 mm, about 10 mm, about 15 mm, about 20 mm, about 25 mm, about 30 mm, about 35 mm, about 40 mm, about 45 mm, or about 50 mm.

Optionally, in some embodiments, metallic elements 116 can be placed along the shaft 110, e.g., around an inner core or support structure (e.g., coils, irrigation lumen 120) of the shaft 110. In some embodiments, the metallic elements 116 can be ferromagnetic components that can be placed near the magnets 112 to enhance the magnetic effects of the magnets 112. For example, the metallic elements 116 can be placed on one or both sides of a magnet 112. In some embodiments, the metallic elements 116 can be composed of iron or an iron alloy. In some embodiments, the metallic elements 116 can include access ports and/or cutouts for receiving electric wire. Such an implementation can provide a pathway to connect lead wires to external electrodes (e.g., shaft electrodes 114). In some embodiments, the metallic elements 116 can have an annular shape.

The catheter 100 can include an irrigation lumen 120 that delivers fluid from a proximal end to a distal end of the catheter 100. In some embodiments, the fluid can include a cooling fluid such as, for example, a saline solution. In some embodiments, the fluid can include a therapeutic agent, e.g., a drug, anesthetic, or other treatment agent. In some embodiments, the irrigation lumen 120 can provide structural support and/or strength for the catheter 100 along its length. For example, the irrigation lumen 120 can be composed of a stretch resistant material, such as a polyimide, a polyimide-filled polytetrafluoroethylene (PTFE), a liquid crystal polymer, or any other stretch resisting material or combinations thereof. In some embodiments, the irrigation lumen 120 can have sufficient stretch resistance, such that the shaft 110 remains intact with application of tensile forces of at least about 15 N, at least about 20 N, at least about 25 N, at least about 30 N, at least about 35 N, at least about 40 N, at least about 45 N, at least about 50 N, at least about 55 N, at least about 60 N, at least about 65 N, at least about 70 N, at least about 75 N, at least about 80 N, at least about 85 N, at least about 90 N, at least about 95 N, or at least about 100 N, inclusive of all values and ranges therebetween.

The distal tip 130 of the catheter 100 can include holes fluidically coupled to the irrigation lumen 120 for delivery of a fluid from the irrigation lumen 120. In some embodiments, the distal tip 130 of the catheter 100 includes magnets 132, electrodes 134, and/or sensors 136. In some embodiments, the distal tip 130 can have a cylindrical or annular shape with the magnets 132, the electrodes 134, and the sensors 136 disposed along a length of the distal tip 130. In some embodiments, the distal tip 130 can include multiple sections spaced apart that are movable relative to each other so that the distal tip 130 can pass through curved sheaths and/or more tortuous patient anatomy more easily than a single, rigid section. In some embodiments, the sensors 136 can include a temperature sensor such as, for example, a thermocouple, disposed in the distal tip 130 for monitoring of the temperature of the distal tip 130 and the immediate surrounding area, e.g., during an ablation procedure. The thermocouple can include, for example, a T-type thermocouple. In some embodiments, the distal tip 130 can include portions that are formed of heat-conductive material, such as, for example, gold, for facilitating temperature measurements via a temperature sensor. For example, an electrode 134 disposed on the distal tip 130 can be formed of gold to facilitate accurate capture of temperature measurements.

In some embodiments, the distal tip 130 can include about 1, about 2, about 3, about 4, about 5, about 6, about 7, about 8, about 9, or about 10 magnets 132, inclusive of all values and ranges therebetween. In some embodiments, the distal tip 130 can include about 1, about 2, about 3, about 4, about 5, about 6, about 7, about 8, about 9, or about 10 electrodes 134, inclusive of all values and ranges therebetween. In some embodiments, the magnets 132 and/or the electrodes 134 can be spaced apart by about 1 mm, about 2 mm, about 3 mm, about 4 mm, about 5 mm, about 6 mm, about 7 mm, about 8 mm, about 9 mm, or about 10 mm, inclusive of all values and ranges therebetween. In some embodiments, the magnets 132 and/or the electrodes 134 can have variable spacing. In other words, a space between a first electrode 134 and a second electrode 134 can be a first distance and a space between a second electrode 134 and a third electrode 134 can be a second distance, the second distance different from the first distance. In some embodiments, the distal tip 130 can include four electrodes 134. The four electrodes 134 can be spaced apart in a 2 mm-5 mm-2 mm spacing scheme. In other words, the spacing between the first electrode 134 and the second electrode 134 can be 2 mm, the spacing between the second electrode 134 and the third electrode 134 can be 5 mm, and the spacing between the third electrode 134 and the fourth electrode 134 can be 2 mm.

Such spacing can provide sensing capability that allows the electrical activity of the heart to be measured and evaluated.

In some embodiments, the distal tip 130 can have a length of at least about 2 mm, at least about 3 mm, at least about 4 mm, at least about 5 mm, at least about 6 mm, at least about 7 mm, at least about 8 mm, at least about 9 mm, at least about 1 cm, at least about 1.5 cm, at least about 2 cm, at least about 2.5 cm, at least about 3 cm, at least about 3.5 cm, at least about 4 cm, or at least about 4.5 cm. In some embodiments, the distal tip 130 can have a length of no more than about 5 cm, no more than about 4.5 cm, no more than about 4 cm, no more than about 3.5 cm, no more than about 3 cm, no more than about 2.5 cm, no more than about 2 cm, no more than about 1.5 cm, no more than about 1 cm, no more than about 9 mm, no more than about 8 mm, no more than about 7 mm, no more than about 6 mm, no more than about 5 mm, no more than about 4 mm, or no more than about 3 mm. Combinations of the above-referenced lengths of the distal tip 130 are also possible (e.g., at least about 2 mm and no more than about 5 cm or at least about 5 mm and no more than about 1 cm), inclusive of all values and ranges therebetween. In some embodiments, the distal tip 130 can have a length of about 2 mm, about 3 mm, about 4 mm, about 5 mm, about 6 mm, about 7 mm, about 8 mm, about 9 mm, about 1 cm, about 1.5 cm, about 2 cm, about 2.5 cm, about 3 cm, about 3.5 cm, about 4 cm, about 4.5 cm, or about 5 cm.

In some embodiments, the electrode(s) 134 can include one or more electrodes 134 that can provide positioning or localization information of the catheter 100 during its operation. In some embodiments, the electrodes 134 can include one or more electrodes 134 (e.g., measurement electrodes) that can be used for mapping of a region of a patient anatomy (e.g., a heart or cardiac chamber of the heart). In some embodiments, the arrangement of the electrodes 134 can allow for intracardiac signals to be captured for cardiac mapping and/or monitoring. In some embodiments, the electrodes 134 can include an electrode 134 for applying a treatment to tissue. The treatment can be, for example, delivery of ablation energy to tissue. Examples of suitable forms of ablation energy can include radiofrequency (RF) energy, irreversible electroporation (IRE) or pulsed field ablation energy, etc. In some embodiments, the electrodes 134 can include ring electrodes. In some embodiments, the electrodes 134 can include one electrode disposed on the distal end of the distal tip 130 (e.g., a tip electrode) and additional electrodes disposed proximal of the distal end of the distal tip 130.

In some embodiments, the tip electrode 134 can partially or fully encapsulate or surround a sensor 136 (e.g., a temperature sensor). In such embodiments, the tip electrode 134 can be configured to relay information or carry signals to the sensor 136. For example, the tip electrode 134 can be formed of gold or another thermally conductive material to enable a temperature sensor 136 disposed within the electrode to capture a temperature of surrounding tissue. In some embodiments, the temperature at the distal end of the distal tip 130 can be constantly monitored (e.g., via the temperature sensor 136). In some embodiments, the tip electrode 134 can have sufficient dimensions to apply RF energy to ablate surrounding tissue in contact with the tip electrode 134. In some embodiments, the tip electrode 134 and/or one or more proximal electrodes 134 can be configured in a monopolar or bipolar arrangement to deliver ablation energy to surrounding tissue, e.g., via RF or IRE. During delivery of ablation energy, it can be desirable to monitor the temperature of the tissue to ensure that the tissue remains within a predetermined range of temperatures or below a predetermined threshold. Optionally, cooling via fluid (e.g., delivered via irrigation lumen 120) and/or cooling elements disposed at the distal tip 130 can be implemented to reduce temperatures in response to determining that the surrounding temperatures have exceeded the predetermined range or threshold.

FIG. 2 is a block diagram of a guiding system including a magnetically steerable catheter 200, according to an embodiment. As shown, the dotted lines represent fluidic couplings, electromagnetic communication, and/or electronic communication between components. The catheter 200 can include components that are structurally and/or functionally similar to the catheter 100, as described above. For example, the catheter 200 includes magnets 212, electrodes 214, sensors 216, and an irrigation lumen 220. In some embodiments, the magnets 212, the electrodes 214, the sensors 216, and the irrigation lumen 220 can be the same or substantially similar to the magnets 112, the electrodes 114, the sensors 136, and the irrigation lumen 120, as described above with reference to FIG. 1. Thus, certain aspects of the magnets 212, the electrodes 214, the sensors 216, and the irrigation lumen 220 are not described in greater detail herein. The magnets 212 can refer to both magnets dispersed throughout the shaft of the catheter 200 (e.g., the magnets 112, as described above with reference to FIG. 1) and the magnets disposed in a distal tip of the catheter 200 (e.g., the magnets 132, as described above with reference to FIG. 1). The electrodes 214 can refer to both electrodes dispersed throughout the shaft of the catheter 200 (e.g., the electrodes 114, as described above with reference to FIG. 1) and the electrodes disposed in the distal tip of the catheter 200 (e.g., the electrodes 134, as described above with reference to FIG. 1).

The magnets 212 can be disposed along a distal portion of the catheter 200 and used to drive movement of the catheter 200 along a predetermined pathway. A magnetic field generator 250 can be configured to generate an external magnetic field that can drive movement of the magnets 212, thereby driving movement of the catheter 200. The generated magnetic field can have a direction orientated for steering a distal tip of the catheter 200 via the magnets 212 in a predefined direction and/or along a predefined pathway. The magnetic field generator 250 can steer and move the magnets 212 from a current position to a desired position. Specific examples of steering via magnets are described in greater detail in, for example, U.S. Pat. No. 8,162,920 ("the '920 patent"), filed Apr. 23, 2004, entitled "Magnetic Navigation of Medical Devices in Magnetic Fields," U.S. Pat. No. 7,161,453 ("the '453 patent"), filed Dec. 7, 2005, entitled "Rotating and Pivoting Magnet for Magnetic Navigation," and U.S. Pat. No. 7,966,059 ("the '059 patent"), filed Jan. 26, 2007, entitled "Rotating and Pivoting Magnet for Magnetic Navigation," the disclosures of which are hereby incorporated by reference in their entirety.

In some embodiments, one or more electrodes 214 and/or sensors 216 can measure signals that can be used to localize the catheter 200 during its movement. For example, an electromagnetic field generator (e.g., magnetic field generator 250 or separate generator) can be used to generate electric and/or magnetic fields that can cause signals to be received at the one or more electrodes 214 and/or sensors 216. These signals can then be used to localize the catheter 200 as it is being navigated through patient anatomy, e.g., via the magnets 212. For example, the signals from the electrodes 214 can be routed to a mapping/sensing system 270, which can use such signals to determine a position and/or orientation of the catheter 200 within the patient anatomy, as further described below.

An ablation signal generator 260 can be operatively coupled to one or more of the electrodes 214, e.g., for generating a voltage or current signal suitable for ablation. A mapping/sensing system or systems 270 can be operatively coupled to one or more of the electrodes 214 and/or the sensors 216, and can be configured to send and/or receive signals from the electrodes 214 and/or the sensors 216. Such signals can be used to determine a position and/or orientation of a portion of the catheter 200 (e.g., a distal tip of the catheter 200), to map a portion of the patient anatomy (e.g., a heart or cardiac chamber of the heart), to monitor physiological signals of the patient (e.g., electrocardiograms (ECGs)), to monitor temperature or other conditions near a treatment site, etc.

A fluid delivery system 280 can be fluidically coupled to the irrigation lumen 220. The fluid delivery system 280 can be configured to control delivery of a gas, liquid, or other substance via irrigation lumen 220 into the patient anatomy. The fluid delivery system 280 delivers fluid through the irrigation lumen 220 and out the distal end of the catheter 200. In some embodiments, the fluid delivery system 280 can include a reservoir of fluid. In some embodiments, the fluid can include a saline solution, a drug solution, an anesthetic, etc. The fluid delivery system 280 can deliver fluid to irrigate and cool the ablation site. In some embodiments, the fluid delivery system 280 can include a pump. In some embodiments, the fluid can be delivered while ablation is occurring. For example, the fluid delivery system 280 can be controlled, e.g., via a processor or control unit, to deliver fluid during predefined periods of time. A temperature sensor 216 can be used to monitor a temperature of a treatment site and to send temperature data to a processor or control unit, which can then control the fluid delivery system 280 to deliver a fluid as necessary to cool and/or heat the treatment site. In some embodiments, the cooling and/or heating properties of the catheter 200 can allow for increased penetration of ablation energy, improving the efficacy of the ablation procedure or a depth of lesion formation.

In some embodiments, the magnetic field generator 250, mapping/sensing system(s) 270, and/or other components of the system can form or be part of a robotic system.

Figure 3:
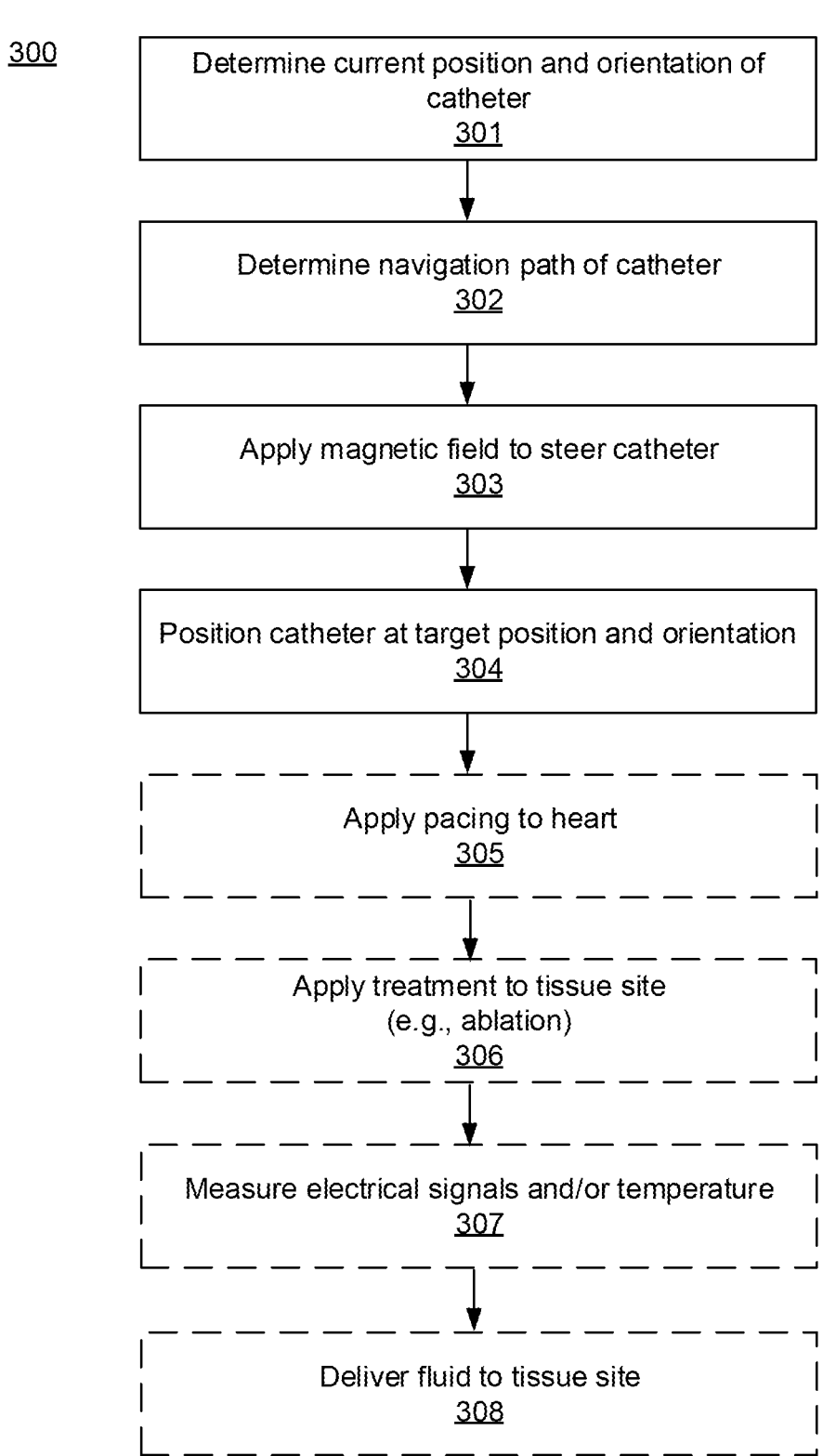
FIG. 3 is a block diagram of a method of operating a magnetically steerable catheter, according to an embodiment.

FIG. 3 shows a block diagram of a method 300 of operating a magnetically steerable catheter, according to an embodiment. As shown, the method 300 includes determining the current position and orientation of a catheter (e.g., any of the catheter as described herein, including catheter 100 and/or 200) at 301, determining a navigation path of the catheter at 302, applying a magnetic field to steer the catheter at 303, and positioning the catheter at a target position and orientation at 304. The method 300 optionally includes applying a pacing to the heart at 305, applying a treatment (e.g., ablation) to a tissue site at 306, measuring electrical signals and/or temperature at 307, and/or irrigating a tissue site at 308.

Determining the current position and orientation of the catheter, at 301, can involve the use of a localization system in combination with one or more sensors disposed on the catheter. For example, an external field generator (e.g., magnetic field generator 250 or a separate electromagnetic field generator) can be used to generate one or more external fields, and one or more sensors disposed on the catheter (e.g., an electrode 114, 134, 214 or a sensor 136, 216) can measure signals in response to the external fields. Such signals can then be communicated to a control unit or processor (e.g., of a mapping/sensing system 270) and used to determine a position and/or orientation of the catheter relative to patient anatomical structures. In some embodiments, such signals can be used to determine the position of the distal tip of the catheter. In some embodiments, such signals can be used to determine the position and/or orientation of magnets, electrodes, and/or other components of the catheter.

At 302, the navigation path of the catheter can be determined based on information of the patient anatomy and/or information associated with a medical procedure. In some embodiments, the navigation path can be selected to minimize or reduce contact between the catheter and sensitive anatomy of a patient (e.g., heart valves, blood vessel walls, etc.). In some embodiments, image data of patient anatomy and/or mapping data (e.g., collected via electrodes 114, 134, 214 and provided to a mapping/sensing system 270) can be used to determine a specific pathway for navigating to a target site in a particular patient. At 303, a magnetic field can be applied (e.g., via magnetic field generator 250) to steer the catheter along the navigation path, e.g., by inducing movement in the magnets (e.g., magnets 112, 132, 212) of the catheter.

The method 300 further includes positioning the catheter at a target position and orientation, at 304. In some embodiments, the catheter can be placed in a target position and/or orientation such that a distal tip of the catheter makes contact with a target location (e.g., treatment site or point) within the patient anatomy (e.g., within the heart). In some embodiments, the catheter can be placed at a specific orientation relative to a surface of the tissue, e.g., to increase contact between a distal tip electrode and the tissue surface and/or to increase depth of penetration of subsequently applied treatment (e.g., RF or IRE ablation). At 305, pacing can optionally be applied to the heart (e.g., to control timing of a cardiac cycle of the heart). In some embodiments, cardiac pacing can be applied using a cardiac stimulator with one or more pacing electrodes. The pacing can involve application of a series of pacing signals, e.g., generated by the cardiac stimulator. The pacing signals can have a duration of about 40 0.1 ms to about 1 ms, inclusive of all values and ranges therebetween. In some embodiments, the pacing signal can have an intensity of about 2 V to about 5 V, inclusive of all values and ranges therebetween.

Optionally, the method 300 can include applying a treatment to a tissue site, step 306. In some embodiments, the treatment can include ablation. The ablation can be applied, for example, using one or more electrodes disposed at a distal tip of the catheter (e.g., one or more electrodes 134). In some embodiments, the ablation can include RF ablation forming lesions in select portions of cardiac tissue. For example, RF ablation can be applied to form transmural lesions in cardiac tissue at one or more pulmonary veins. In some embodiments, the power of the RF energy being used can be about 10 W to about 100 W, inclusive of all values and ranges therebetween. In some embodiments, the ablation can include IRE ablation or pulsed field ablation. In some embodiments, the ablation can include thermal ablation. In some embodiments, the ablation can include cryogenic ablation. In some embodiments, the ablation can include chemical ablation.

Optionally, the method 300 can include measuring electrical signals, temperature, and/or other information, at 307. In some embodiments, the measurement can be via sensors (e.g., an electrode 114, 134, 214 or a sensor 136, 216). In some embodiments, adjustments can be made in response to the electrical signals and/or temperature measurements at

307. In some embodiments, these adjustments can include adjusting an ablation procedure (e.g., applying more or less current or voltage for ablation) or terminating an ablation procedure, applying more or less fluid to a tissue site (e.g., to cool or heat the tissue site), and/or any other appropriate adjustments. Such adjustments can be made via a control unit or processor that is operatively coupled to the various components of the catheter, as described with reference to FIGS. 1 and 2.

Optionally, the method 300 can include delivering fluid to a tissue site, e.g., using a fluid delivery system 280 and/or an irrigation lumen 120, 220, at 308. This can include delivery of fluid for clearing dead tissue and other debris, e.g., to improve penetration of ablation energy. In some embodiments, one or more therapeutic agents can also be delivered to a tissue site, e.g., to improve or enhance an ablation procedure. In some embodiments, the irrigation fluid can be used to cool the tissue site. For example, the irrigation system can provide cooling during ablation energy delivery. This can allow for temperature control and, together with a temperature sensor, precise temperature monitoring to avoid overheating or carbonization of the tissue during an ablation procedure.

Figure 4:
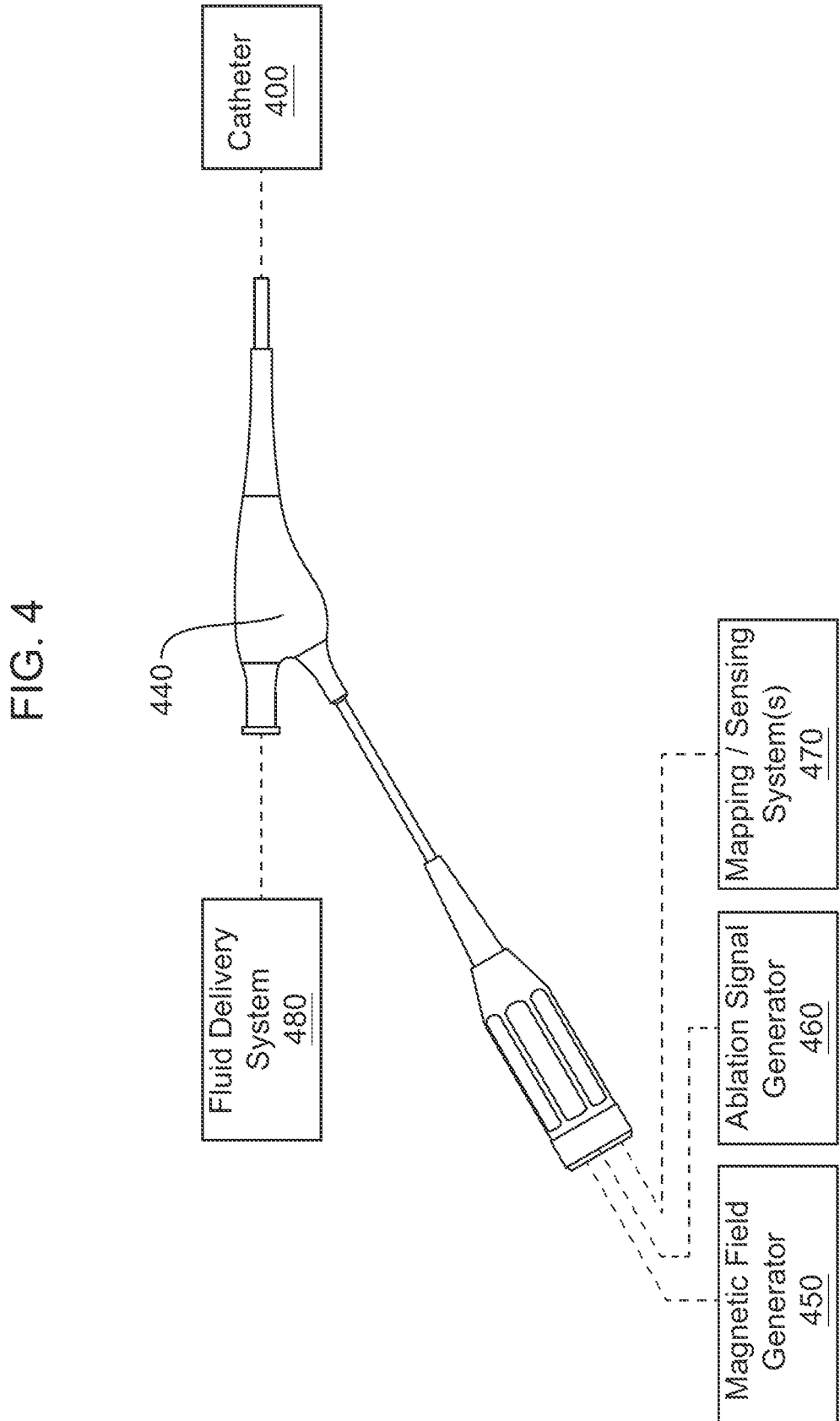
FIG. 4 is an illustration of a connector for a magnetically steerable catheter, according to an embodiment.

FIG. 4 is an illustration of a connector 440 for a magnetically steerable catheter, according to an embodiment. The connector 440 can include multiple ports and/or connections that enable connection to a plurality of devices and/or systems. For example, FIG. 4 shows how the connector 440 can connect the catheter 400 to a fluid delivery system 480. FIG. 4 also shows how the connector 440 can connect the catheter 400 to a magnetic field generator 450, an ablation signal generator 460, a mapping/sensing system(s) 470, and a fluid delivery system 480. As shown, the connector 440 can be located at a proximal end of the catheter 400, with a shaft of the catheter 400 extending distally from the connector 440. In some embodiments, the connector 440 can be a Y-connector.

The connection between the connector 440 and the magnetic field generator 450, the ablation signal generator 460, or the mapping/sensing system(s) 470 can be an electronic connection, e.g., via one or more electronic connectors and/or cables. In some embodiments, one or more cables can be disposed in the connector 440 to connect the magnetic field generator 450, the ablation signal generator 460, and the mapping/sensing system(s) 470 to the catheter 400. In some embodiments, the catheter 400, the magnetic field generator 450, the ablation signal generator 460, the mapping/sensing system(s) 470, and the fluid delivery system 480 can be the same or substantially similar to the catheter 100, 200, the magnetic field generator 250, the ablation signal generator 260, the mapping/sensing system(s) 270, and the fluid delivery system 280, as described above with reference to FIGS. 1 and 2. Thus, certain aspects of the catheter 400, the magnetic field generator 450, the ablation signal generator 460, the mapping/sensing system(s) 470, and the fluid delivery system 480 are not described in greater detail herein.

In some embodiments, the connector 440 can be connected to the fluid delivery system 480 via a hose or fluid line. In some embodiments, the catheter 400 can have an irrigation lumen (e.g., irrigation lumen 120, 220) that can extend from a distal end of the catheter 400 to a Luer lock adapter or other connection disposed in the connector 440. Alternatively, the connector 440 can have a separate lumen or channel disposed therein that connects to an irrigation lumen of the catheter 400 and to a fluid line of the fluid delivery system 480.

Figure 5A:
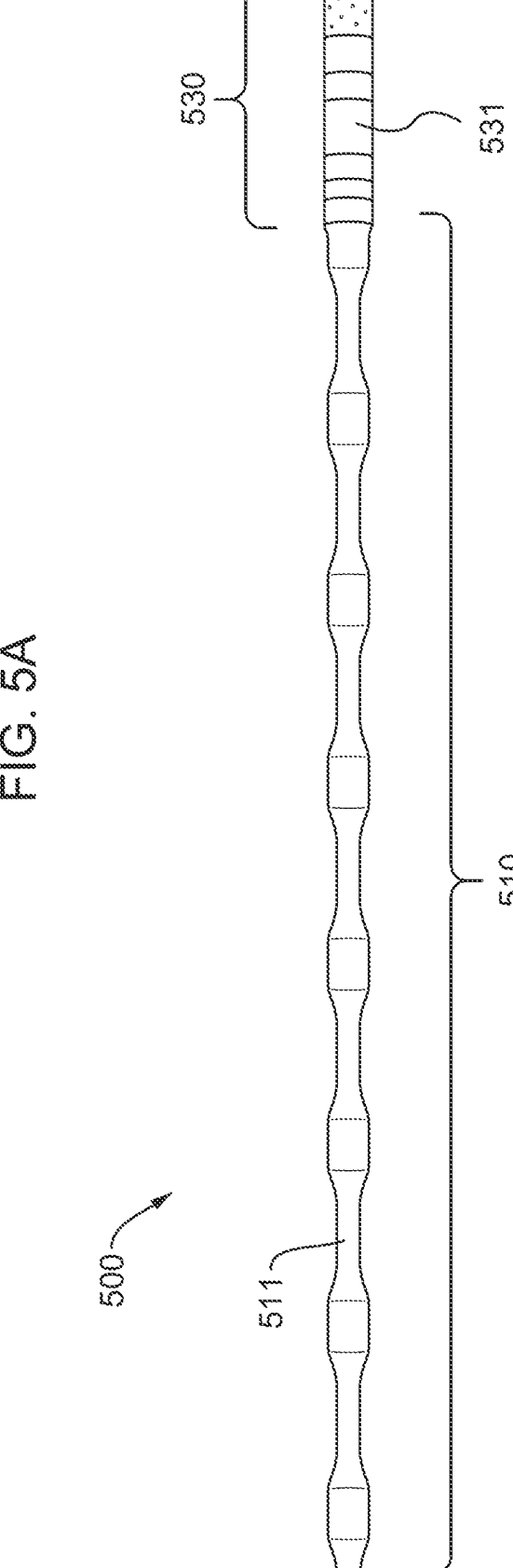
FIGS. 5A-5B are illustrations of a magnetically steerable catheter, according to an embodiment.
Figure 5B:
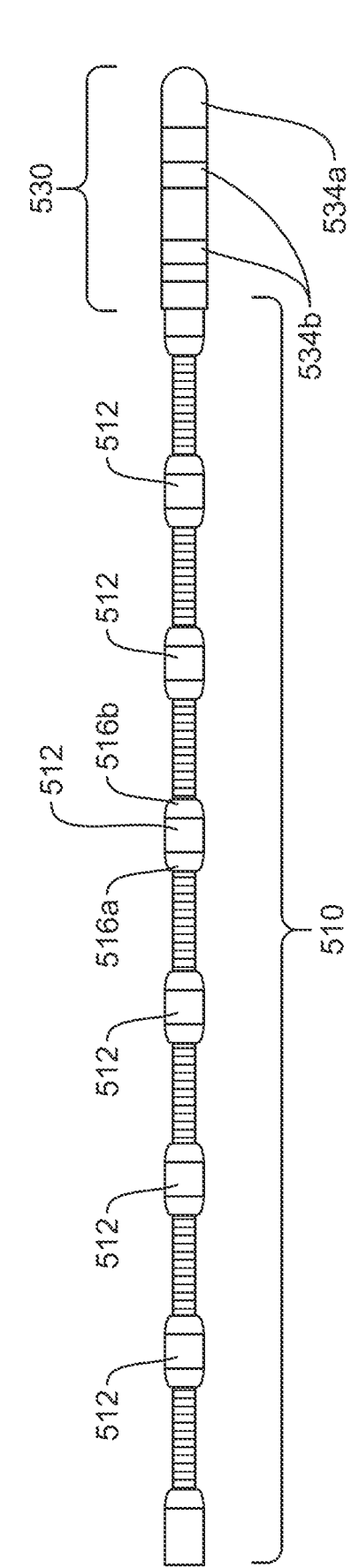
Figure 6:
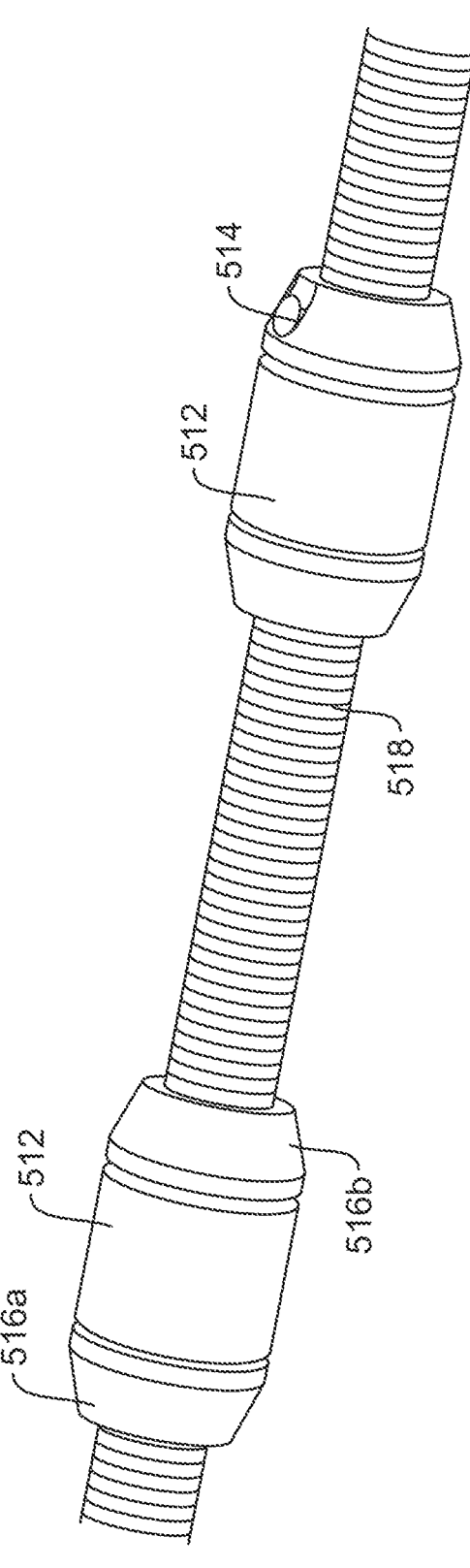
FIG. 6 is an illustration of magnets from a magnetically steerable catheter, according to an embodiment.
Figure 7A:
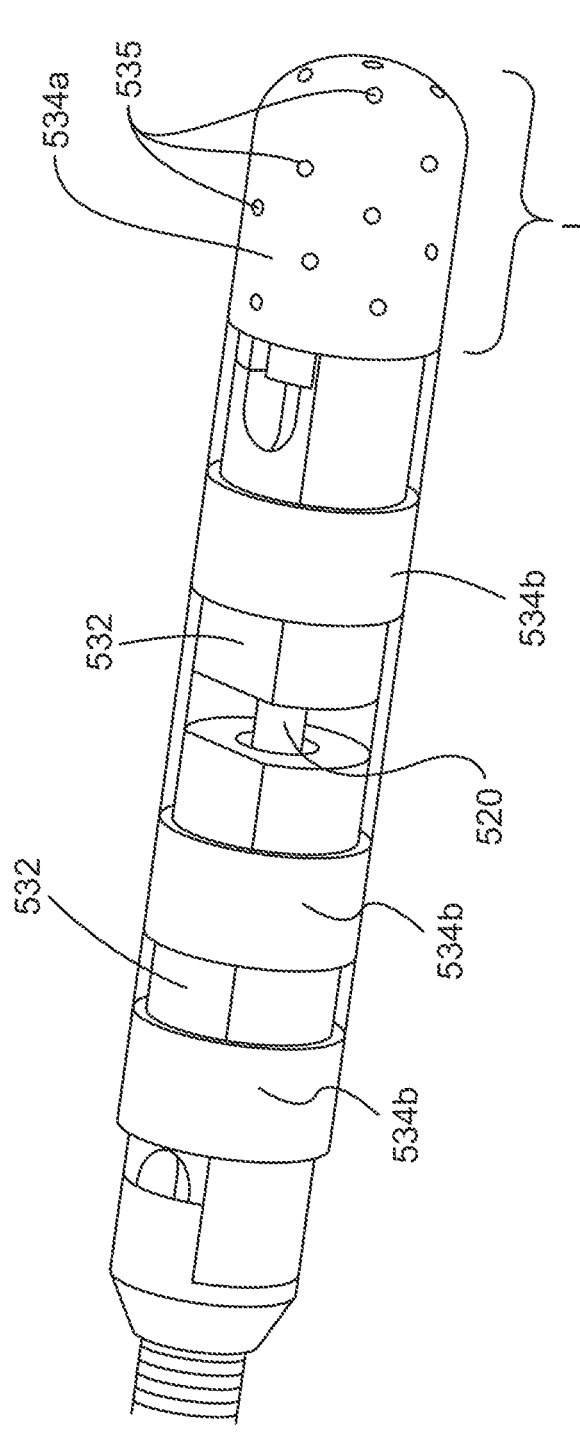
Figure 7B:
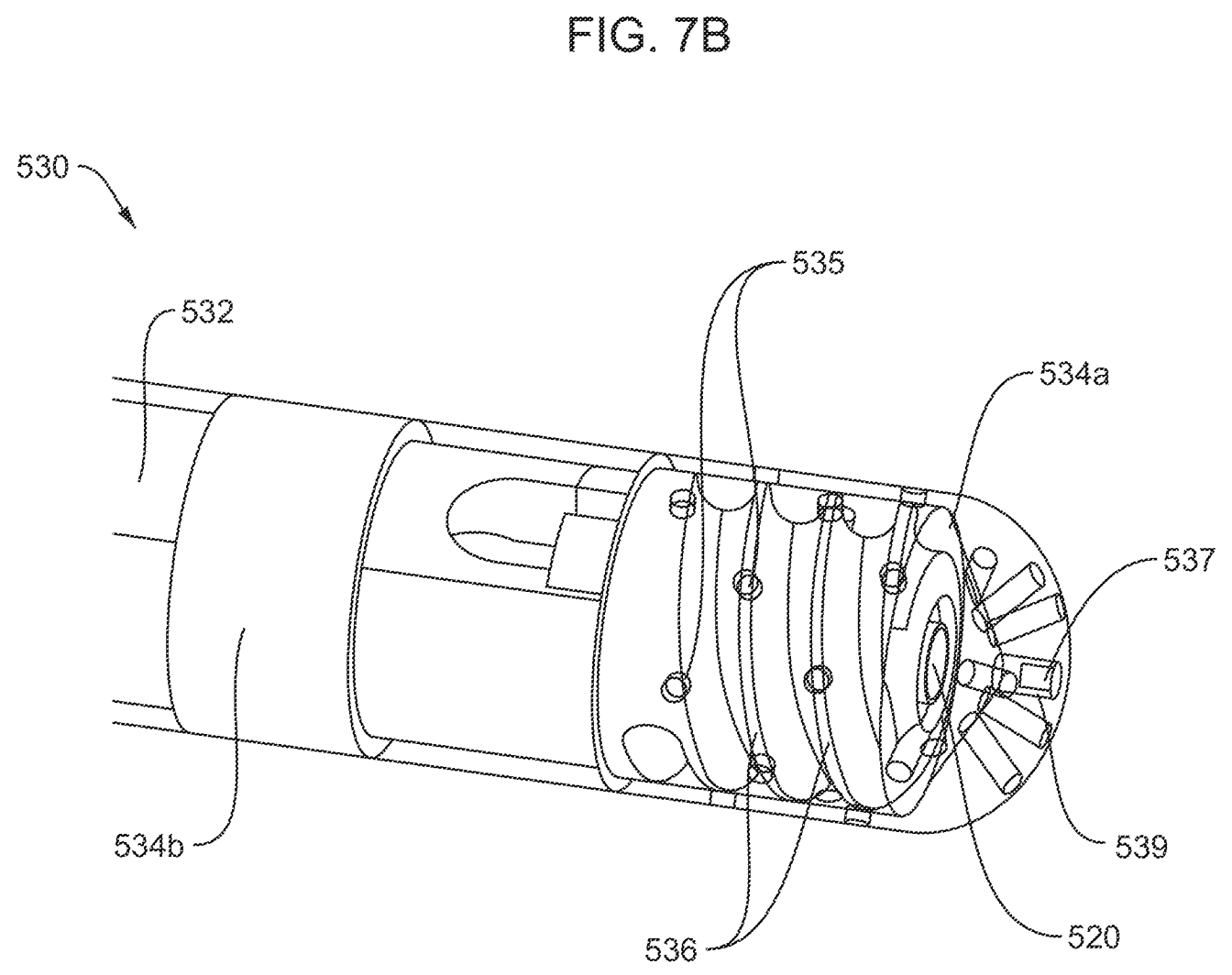

FIGS. 5A-7B show illustrations of a catheter 500, and various components thereof, according to an embodiment. As shown, the catheter 500 includes a shaft 510, a shaft jacket or sleeve 511, magnets 512, electrodes 514, metallic elements 516a, 516b (collectively referred to as metallic elements 516), coils 518, an irrigation lumen 520, and a distal tip 530 with distal tip jacket or sleeve 531, magnets 532, electrodes 534a, 534b (collectively referred to as electrodes 534), holes 535, a helical distribution member 536, and a temperature sensor 537. FIG. 5A shows the catheter 500 with the shaft jacket 511 disposed thereon, while FIG. 5B shows the catheter 500 with the shaft jacket 511 removed. FIG. 6 shows a detailed view of two of the magnets 512, one of the electrodes 514, and the metallic elements 516. FIG. 7A shows a detailed view of the distal tip 530 of the catheter 500, while FIG. 7B shows a detailed view of the distal end of the distal tip 530 with the electrode 534a made transparent to illustrate the interior of the distal tip 530. The catheter 500 can be structurally and/or functionally similar to other catheters described herein, and therefore include similar components as other catheters and/or be coupled to similar systems and/or components as other catheters (e.g., magnetic field generators, ablation signal generators, mapping/sensing systems, fluid delivery systems, etc.). For example, the shaft 510, the magnets 512, the electrodes 514, the metallic elements 516, the irrigation lumen 520, the distal tip 530, the magnets 532, and the electrodes 534 can be the same or substantially similar to the shaft 110, the magnets 112, 212, the electrodes 114, 214, the metallic elements 116, the irrigation lumen 120, 220, the distal tip 130, the magnets 132, and the electrodes 134, as described above with reference to FIGS. 1 and 2. Thus, certain aspects of the shaft 510, the magnets 512, the electrodes 514, the metallic elements 516, the irrigation lumen 520, the distal tip 530, the magnets 532, and the electrodes 534 are not described in greater detail herein.

While not depicted, the shaft 510 can be coupled at its proximal end to a connector, such as, for example, connector 440 described with reference to FIG. 4. The shaft 510 can include a shaft jacket or sleeve 511 that can be disposed around the outside of the shaft 510, e.g., to protect internal components of the shaft 510 (e.g., magnets) and/or to prevent unwanted contact between patient anatomy and portion(s) of the catheter 500 that are not biocompatible. In some embodiments, the shaft jacket 511 can be configured to reduce friction or increase smoothness along an exterior of the shaft 510 (e.g., to provide a smooth external surface for the shaft 510) such that the shaft 510 can be navigated through delivery sheaths and/or patient vasculature with greater ease. In some embodiments, the shaft jacket 511 can also prevent kinking or sharp bending (e.g., discontinuities in a shape of the catheter 500) during navigation. The distal tip 530 can similarly include a jacket or sleeve 531, e.g., for reducing friction and/or discontinuities between various portions of the distal tip 530 and/or to separate internal components of the distal tip 530 (e.g., magnets) from patient anatomy. In some embodiments, the jackets 511 or 531 can be discontinuous at various points or regions along a length of the catheter 500, such that various components of the catheter 500 can be exposed to patient anatomy (e.g., electrodes for ablation and/or sensing). In some embodiments, the shaft jacket 511 and/or the distal tip jacket 531 can be composed of a polymer, an elastomer, a polyamide, Zytel®, Rilsan®, Grilamid®, Vestamid®, Pebax®, or any combination thereof. In some embodiments, the shaft jacket 511 and/or the distal tip jacket 531 can be formed of an insulating material. The shaft jacket 511, the distal tip jacket 531, and/or other components of the catheter 500 (e.g., electrodes) can be at least partially composed of biocompatible materials and make contact with tissues within a patient. The shaft jacket 511 and the distal tip jacket 531 can provide protection to the patient anatomy without inhibiting the steerability of the catheter 500.

FIG. 6 shows a detailed view of the shaft 510 with the shaft jacket 511 removed. Metallic elements 516 can be incorporated into the catheter 500 to facilitate coupling between the magnets 512 and the remaining components of the catheter 500. For example, the magnets 512 are disposed between metallic elements 516. The metallic elements 516 can be magnetically coupled to the magnets 512 and/or coupled via other mechanisms (e.g., adhesives, etc.). The metallic elements 516 can be coupled to coils 518 of the catheter 500 that extend between the metallic elements 516. Because the metallic elements 516 and the coils 518 are formed of metal, the metallic elements 516 and the coils 518 can be welded (e.g., laser welded) together. Alternatively or additionally, the metallic elements 516 and the coils 518 can be coupled via adhesives, fastening elements, friction fit, etc. The coils 518 can be disposed between each magnet and metallic element set (i.e., each grouping of a magnet 512 with two metallic elements 516). Each coil 518 can be coupled at one end to a first metallic element 516 and at a second end to a second metallic element 516. The coils 518 can provide support in those regions without a magnet 512 and/or metallic element 516. The coils 518 terminate at each metallic element 516 and therefore do not extend through the metallic elements 516 or magnets 512. As shown, an electrode 514 can be disposed in a notch or opening in one or more of the metallic elements 516. In some embodiments, the electrodes 514 can be integrated into and/or coupled to one or more of the metallic elements 516 adjacent to each of the magnets 512. In some embodiments, the electrodes 514 can be integrated into and/or coupled to one or more of the metallic elements 516 adjacent to a subset of the magnets 512. In some embodiments, the catheter 500 can have an irrigation lumen 520 disposed within the coils that can prevent the coils 518 and the magnets 512 from being pulled apart, e.g., by having sufficient stretch resistance. Alternatively or additionally, the shaft 510 can have a string or other support structure (not shown) disposed therein to keep the coils 518 from being pulled apart from one another. In some embodiments, the string can be composed of a polymer, a ceramic, Kevlar®, or any combination thereof.

As shown, the irrigation lumen 520 terminates at a point distal to about 80% of the electrode 534a. In other words, the irrigation lumen 520 is shown as terminating with about 80% of the length of the electrode 534a being proximal to the distal end of the irrigation lumen 520 and about 20% of the length of the electrode 534a distal to the distal end of the irrigation lumen 520. In some embodiments, the irrigation lumen 520 can terminate at a point distal to about 10%, about 20%, about 30%, about 40%, about 50%, about 60%, about 70%, about 80%, or about 90% of the electrode 534a, inclusive of all values and ranges therebetween. In some embodiments, the irrigation lumen 520 can terminate at a location proximal to the electrode 534a. Placement of the holes 535 throughout the electrode 534a can enable flow of a fluid delivered via the irrigation lumen 520 to be distributed in multiple directions.

In some embodiments, the metallic elements 516 can have magnetic properties induced by the magnets 512. In other words, the magnets 512 can induce an electric field in the metallic elements 516, such that the metallic elements 516 and the magnets 512 can effectively behave as a larger magnet. In some embodiments, the metallic elements 516 can enhance the strength of the shaft 510.

The magnets 512 can be evenly distributed along a distal portion of the shaft 510, as depicted in FIG. 5B. As depicted in FIG. 5B, the catheter 500 can have six magnets 512 disposed along the shaft 510 and two magnets 532 disposed at a distal tip 530. In some embodiments, the metallic elements 516 can be formed of a ferromagnetic material (e.g., iron), such that the metallic elements 516 can enhance a magnetic strength or magnetic moment of the magnets 512. A magnetic field generator (e.g., magnetic field generator 250, 450) can be used to steer the catheter 500 via the magnets 512 and the magnets 532, as described above with reference to FIGS. 1-4. In some embodiments, the magnets 512, 532 can be sufficient in number such that when a magnetic field is applied to the magnets 512, 532, the distal portion of the catheter 500 carrying the magnets 512, 532 can be configured to curve in a smooth or substantially smooth manner. Stated differently, the distal portion of the catheter 500 can be configured to transition into a curved configuration in response to the application of a magnetic field, in which the distal portion of the catheter 500 has a radius of curvature or is within a range of radii of curvatures (e.g., about 4 mm to about 25 mm, inclusive of all values and ranges therebetween). In some embodiments, the transition of the distal portion of the catheter 500 into a curved configuration in response to the application of a magnetic field can be due to usage and placement of the shaft magnets and a ferromagnetic material. In some embodiments, the radius of curvature can be associated with the internal dimensions of a cardiac chamber of a heart (e.g., a left atrial chamber of the heart). This can allow the distal portion of the catheter 500 carrying the magnets 512, 532 to be configured to fit within the cardiac chamber, e.g., during mapping and/or ablation.

As shown in FIGS. 7A and 7B, the distal tip 530 includes the tip electrode 534a disposed at the distal end of the distal tip 530 with three additional electrodes 534b disposed proximal to the tip electrode 534a. As shown, the distal tip 530 is separated into two sections, a proximal section and a distal section, with the magnets 532 and the electrodes 534 parsed between the two sections. The distal section and the proximal section are moveable relative to one another. In other words, the distal section and the proximal section have a flexible segment disposed therebetween. Separating the distal tip 530 (and the magnets 532 and the electrodes 534) into multiple sections that are movable relative to one another can allow the distal tip 530 to curve during insertion. Such curving can facilitate navigation of the distal tip 530 through bends of a delivery sheath and/or more tortuous patient anatomy. While two sections are disclosed herein, it can be appreciated that the distal tip 530 can be separated into 3, 4, 5, 6, 7, 8, 9, 10, or more than 10 sections, inclusive of all values and ranges therebetween. In some embodiments, one or more of the electrodes 534a, 534b can be configured to collect physiological data from nearby tissue or anatomical structures (e.g., the heart). In some embodiments, one or more of the electrodes 534a, 534b can apply ablation energy (e.g., RF or IRE) to ablate nearby tissue. In some embodiments, a first subset of electrodes 534a, 534b (such as, for example, electrodes 534b) can be configured to collect physiological data, and a second subset of electrodes 534a, 534b (such as, for example, tip electrode 534a) can be configured to apply ablation energy. In some embodiments, one or more of electrodes 534a, 534b can be configured to contact a tissue surface to ablate the tissue, e.g., to apply ablation via RF or IRE. For example, the tip electrode 534a can be configured to contact a tissue surface to ablate the tissue. In other embodiments, the one or more electrodes 534a, 534b can be configured to be placed near tissue but not in contact with tissue, e.g., to apply ablation via IRE.

As shown, the electrode 534a can be a dome-shaped electrode with holes 535 dispersed throughout the electrode 534a for delivery of a fluid (e.g., an irrigation fluid, cooling fluid, drug, therapeutic, etc.). In an embodiment, the electrode 534a includes 25 holes 535. The holes 535 can be evenly distributed to enable even distribution of fluid around a distal end of the catheter 500. In some embodiments, the electrode 534a can include at least about 1 hole 535 to at least about 95 holes 535, inclusive of all values and subranges therebetween. In some embodiments, the electrode 534a can include no more than about 100 holes 535 to no more than about 2 holes 535, inclusive of all values and subranges therebetween. Combinations of the above-referenced numbers of holes 535 are also possible (e.g., at least about 1 hole 535 and no more than about 100 holes 535 or at least about 20 holes 535 and no more than about 50 holes 535), inclusive of all values and ranges therebetween.

In some embodiments, the electrode 534a can have a length L of at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, at least about 7 mm, at least about 7.5 mm, at least about 8 mm, at least about 8.5 mm, at least about 9 mm, or at least about 9.5 mm. In some embodiments, the electrode 534a can have a length of no more than about 10 mm, no more than about 9.5 mm, no more than about 9 mm, no more than about 8.5 mm, no more than about 8 mm, no more than about 7.5 mm, no more than about 7 mm, no more than about 6.5 mm, no more than about 6 mm, no more than about 5.5 mm, no more than about 5 mm, no more than about 4.5 mm, no more than about 4 mm, no more than about 3.5 mm, no more than about 3 mm, no more than about 2.5 mm, no more than about 2 mm, or no more than about 1.5 mm. Combinations of the above-referenced lengths of the electrode 534a are also possible (e.g., at least about 1 mm and no more than about 10 mm or at least about 2 mm and no more than about 5 mm), inclusive of all values and ranges therebetween. In some embodiments, the electrode 534a can have a length of about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 10 mm.

In some embodiments, a helical distribution member 536 can be disposed within the electrode 534a. The helical distribution member 536 can be a coil or other structure that has a helical shape. The helical distribution member 536 can extend along a length of the electrode 534a and be configured to evenly distribute fluid that is delivered to the distal end of the catheter via the irrigation lumen 520. As such, the helical distribution member can be configured to provide even, uniform fluid distribution.

In some embodiments, the catheter 500 can include a temperature sensor 537 that can be disposed near a distal end of the catheter 500. For example, the temperature sensor 537 can be disposed within or near the electrode 534a. In some embodiments, the temperature sensor 537 is disposed a hole of the electrode 534a. The temperature sensor 537 is shown as being integrated into a hole 539 at a distalmost end of the electrode 534a. As shown, the hole 539 at the distalmost end of the electrode 534a can have a cylindrical shape (or generally cylindrical shape) with a longitudinal axis that extends parallel to a longitudinal axis of the irrigation lumen 520. The hole 539 can be configured to have a distal opening that allows entry of blood and/or tissue at least partially into the hole 539. In some embodiments, the temperature sensor 537 can be configured to contact the blood and/or tissue to measure temperature. The temperature sensor 537 can be configured to measure a temperature near the distal end of the catheter 500, e.g., for monitoring temperature during an ablation procedure. In some embodiments, the electrode 534a can be formed of a thermally conductive material (e.g., gold), e.g., to increase the accuracy of the temperature capture. In some embodiments, having the temperature sensor 537 integrated at a distalmost end (or near the distalmost end) of the electrode 534a, and therefore located at a distalmost end (or near the distalmost end) of the catheter 500, can allow the temperature sensor 537 to obtain a temperature measurement that is more representative of an area of tissue being treated. For example, in many applications, the tissue being ablated is tissue that is in contact with or proximate to the distal end of the catheter 500. As such, the temperature sensor 537 by being positioned at the distal end, can facilitate measurements that are more representative of the treated tissue. This can improve the safety of an ablation procedure, as the temperature sensor 537 can be configured to produce more accurate temperature measurements and allow a physician to adjust the ablation procedure appropriately to account for temperatures that are outside of a desirable range (e.g., temperatures that are too high and/or too low). This safety improvement is particularly present if the electrode 534a is composed of a material with a high heat conductivity (e.g., gold). Additionally, placing the temperature sensor 537 in a relatively exposed location (e.g., the hole 535 at the distal end of the electrode 534a) can facilitate physical contact between the temperature sensor 537 and the tissue.

In some embodiments, the catheter 500 can have a shutoff temperature, such that the catheter 500 ceases ablation or reduces an amount of ablation energy (e.g., by reducing a voltage being applied) upon reaching the shutoff temperature. In some embodiments, the shutoff temperature can be predefined by the user. In some embodiments, the shutoff temperature can be between about 30° C. to about 90° C., inclusive of all values and ranges therebetween. As tissue warms up, the temperature sensor 537 can have enhanced performance, as the materials in the electrode 534a (e.g., gold) can transmit heat faster.

As used in this specification, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

The term "substantially" when used in connection with "cylindrical," "linear," and/or other geometric relationships is intended to convey that the structure so defined is nominally cylindrical, linear or the like. As one example, a portion of a support member that is described as being "substantially linear" is intended to convey that, although linearity of the portion is desirable, some non-linearity can occur in a "substantially linear" portion. Such non-linearity can result from manufacturing tolerances, or other practical considerations (such as, for example, the pressure or force applied to the support member). Thus, a geometric construction modified by the term "substantially" includes such geometric properties within a tolerance of plus or minus 5% of the stated geometric construction. For example, a "substantially linear" portion is a portion that defines an axis or center line that is within plus or minus 5% of being linear.

As used herein, the term "set" and "plurality" can refer to multiple features or a singular feature with multiple parts. For example, when referring to a set of magnets, the set of magnets can be considered as one magnet with multiple portions, or the set of magnets can be considered as multiple, distinct magnets. Additionally, for example, when referring to a plurality of electrodes, the plurality of electrodes can be considered as multiple, distinct electrodes cells or as one electrode with multiple portions. Thus, a set of portions or a plurality of portions may include multiple portions that are either continuous or discontinuous from each other. A plurality of particles or a plurality of materials can also be fabricated from multiple items that are produced separately and are later joined together (e.g., via mixing, an adhesive, or any suitable method).

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of" or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A steerable catheter, comprising:
a distal tip including a first set of magnets; and
a shaft including:
   a flexible section having a distal end coupled to the distal tip;
   a second set of magnets disposed on the flexible section, the second set of magnets being spaced along a length of the flexible section and being spaced from the first set of magnets such that the first and second sets of magnets collectively enable the flexible section to curve without kinking in response to a magnetic field being applied to the first and second sets of magnets; and
   a set of coils disposed on the flexible section, each coil disposed between adjacent magnets of the second set of magnets,
   each magnet from the second set of magnets being coupled to each coil from the set of coils via metallic elements disposed at the ends of each magnet.

2. The steerable catheter of claim 1, wherein each metallic element is formed of a ferromagnetic material.

3. The steerable catheter of claim 1, wherein the first set of magnets is separated into at least two sections with a flexible element in between, the flexible element configured to allow the distal tip to curve.

4. The steerable catheter of claim 1, wherein the distal tip includes a treatment electrode configured to apply a treatment to a tissue site.

5. The steerable catheter of claim 4, wherein the treatment electrode is configured to apply at least one of: radiofrequency (RF) energy to ablate tissue at the tissue site, or pulsed field energy to irreversibly electroporate tissue at the tissue site.

6. The steerable catheter of claim 4, wherein the treatment electrode includes a tip electrode having a set of irrigation openings, the steerable catheter further including:
   an irrigation lumen extending from a proximal end of the shaft to the tip electrode, the irrigation lumen configured to convey a fluid to the set of irrigation openings such that the fluid can be delivered to the tissue site.

7. The steerable catheter of claim 6, wherein the tip electrode includes a helical distribution member that is configured to distribute the fluid substantially evenly to the set of irrigation openings.

8. The steerable catheter of claim 6, wherein the irrigation lumen has sufficient stretch resistance such that the shaft remains intact with application of tensile forces greater than or equal to about 15 N.

9. The steerable catheter of claim 1, wherein the distal tip includes a measurement electrode configured to measure electrical signals for at least one of: diagnosis of biological data, localization of the distal tip, or mapping of a region of patient anatomy.

10. The steerable catheter of claim 1, further comprising:
a set of electrodes disposed along the flexible section of the shaft.

11. The steerable catheter of claim 10, wherein each electrode from the set of electrodes is disposed adjacent to a magnet from the second set of magnets.

12. The steerable catheter of claim 1, wherein the distal tip includes a temperature sensor configured to sense a temperature of tissue near the distal tip.

13. The steerable catheter of claim 1, wherein the flexible section is configured to curve to fit within a heart chamber.

14. The steerable catheter of claim 1, wherein the second set of magnets is evenly distributed along the length of the flexible section of the shaft.

\* \* \* \* \*